United States Patent [19]

Chan

[11] Patent Number: 4,468,247

[45] Date of Patent: Aug. 28, 1984

[54] HERBICIDAL 4-[3'-(4"-TRIFLUOROMETHYL-PHENOXY)-PHENOXY]-4-METHYL-CROTONATES

[75] Inventor: David C. K. Chan, Petaluma, Calif.

[73] Assignee: Chevron Research Company, San Francisco, Calif.

[21] Appl. No.: 391,022

[22] Filed: Jun. 22, 1982

Related U.S. Application Data

[63] Continuation of Ser. No. 158,039, Jun. 9, 1980, abandoned.

[51] Int. Cl.$^3$ .................... A01N 37/06; C07C 69/76
[52] U.S. Cl. ........................................ 71/108; 71/116; 560/62; 562/472
[58] Field of Search .................. 71/108, 116; 560/62; 562/472

[56] References Cited

U.S. PATENT DOCUMENTS 4,163,661  8/1979  Jikibara et al. ................. 71/108

Primary Examiner—Catherine L. Mills
Attorney, Agent, or Firm—S. R. LaPaglia; T. G. DeJonghe; L. S. Squires

[57] ABSTRACT

Salts, esters, amides, hydrazides and hydroxyamides of 4-methyl-4-[3'-(4"-trifluoromethylphenoxy)-phenoxy]-crotonic acid are herbicidal against broad leaf plants.

10 Claims, No Drawings

HERBICIDAL 4-[3'-(4''-TRIFLUOROMETHYL-PHENOXY)-PHENOXY]-4-METHYL-CROTONATES

This is a continuation of application Ser. No. 158,039, filed June 9, 1980 now abandoned.

BACKGROUND OF THE INVENTION

U.S. Pat. No. 4,163,661 discloses grass herbicides which are alkyl esters of 4-methyl-4-[4'-(4'''-trifluoromethyl-phenoxy)-phenoxy]-crotonic acid.

U.S. Pat. No. 4,134,753 discloses herbicidal 4-halo-4'-nitro-3'-alkanoyloxy-diphenyl ethers.

U.S. Pat. No. 4,093,446 discloses herbicidal 4-trifluoromethyl-4'-nitro-diphenyl ethers.

SUMMARY OF THE INVENTION

This invention relates to novel herbicidal compounds, compositions and method of use thereof. It has been found that 4-[3'-(4''-trifluoromethyl-phenoxy)-phenoxy]-crotonic acid derivatives have broad leaf herbicidal activity.

DESCRIPTION OF THE INVENTION

The compounds of the invention have the formula (I):

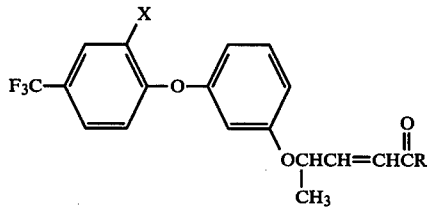

wherein X is hydrogen or halo and R is —OR$^1$, —NR$^1$R$^2$, —NR$^1$NR$^2$R$^3$, —NR$^1$OR$^2$ or —OM; M is a monovalent inorganic cation or quaternary ammonium cation; and R$^1$, R$^2$ and R$^3$ are individually hydrogen, alkyl of 1 to 6 carbon atoms, alkenyl of 2 to 6 carbon atoms or alkynyl of 2 to 6 carbon atoms.

Representative X groups are hydrogen, chloro, bromo, fluoro and iodo. Preferably, X is chloro or hydrogen. Most preferably X is chloro.

Representative R groups are hydroxy, methoxy, ethoxy, i-propoxy, n-propoxy, n-butoxy, i-butoxy, sec-butoxy, n-pentoxy, i-pentoxy, neo-pentoxy, n-hexoxy, amino, methylamino, dimethylamino, diethylamino, methylethylamino, allylamino, propargylamino, hydrazino, 2,2-dimethylhydrazino, 1,2-dimethylhydrazino, 2,2-diethylhyrazino, hydroxylamino, methoxyamino, ethoxyamino, N-methyl-methoxyamino, —O$^-$Na$^+$, —O$^-$K$^+$, —$^O-$(CH$_3$)$_4$N$^+$, —O$^-$(C$_2$H$_4$)$_4$N$^+$.

Preferably, R is hydroxy, and —OM and alkoxy of 1 to 6 carbon atoms. Most preferably R is ethoxy.

The compounds of the invention may be prepared according to the following scheme:

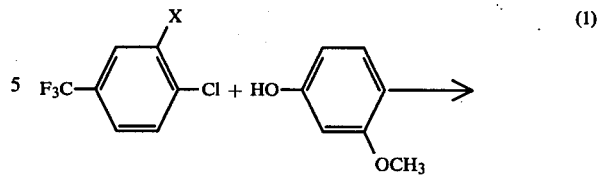

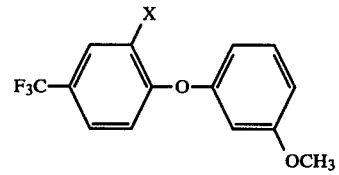

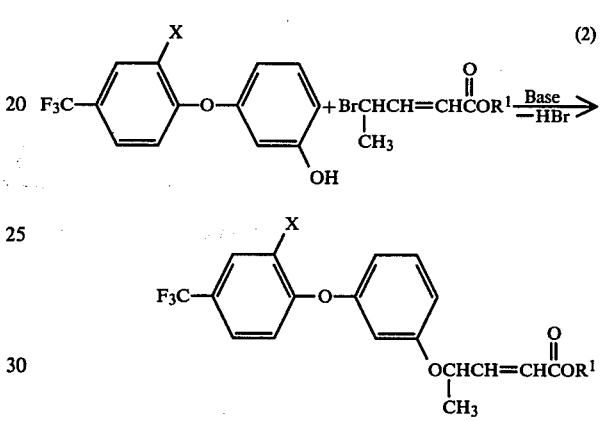

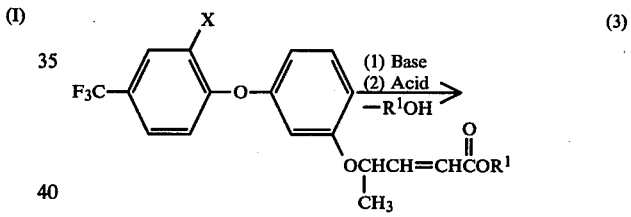

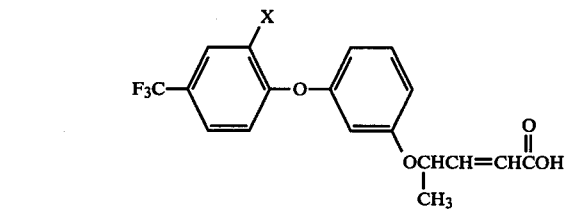

Reaction (1) is a conventional coupling reaction and is conducted by first generating the phenoxide salt of m-methoxy anisole by treatment with a strong base such as potassium hydroxide or sodium hydride. This may be done at ambient temperature in a non-hydrogen donating solvent, such as, dimethylsulfoxide, preferably under inert atmosphere and anhydrous conditions. The chlorobenzene reactant may be reacted with the phenoxide salt at from about 100°–200° C., also under anhydrous conditions. The resulting O-methyl ether may be demethylated by treatment with trialkylsilane chloride and sodium iodide in a nonhydrogen donating solvent, preferably acetonitrile, at 20°–60° C., under inert atmosphere, followed by treatment with a hydrogen donating compound, such as water or alcohol.

Reaction (2) may be conducted by first generating the phenoxide salt of the diphenyl ether by treatment with a base, such as potassium hydroxide or carbonate and then reacting the phenoxide salt with the bromopentenoic ester. Preferably the reaction is conducted under inert atmosphere in an inert diluent at from 20°–100° C.

Reaction (3) is a conventional hydrolysis in base, preferably sodium hydroxide, followed by acidification to isolate the desired acid.

Reaction (4) is shown as a conventional conversion of a carboxylic acid to an amide by first treatment with oxalyl chloride, followed by treatment with an amine. Any suitable reagent may be used to generate the acid chloride, such as, thionyl chloride, oxalyl chloride or phosphorus tri- and penta-halides. The reaction may be conducted at ambient temperatures in a suitable inert diluent, such as ethers or halogenated alkanes.

All of the above intermediates and products may be purified by conventional methods, such as crystallization and chromatography, and are identified by infrared and nmr spectroscopy, elemental analysis and physical characteristics, such as color, and melting or boiling point.

UTILITY

The compounds of the present invention are, in general, herbicidal in both pre- and post-emergent applications. For pre-emergent control of undesirable vegetation, the herbidical compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are particularly effective against broad-leaved weeds. Some may be selective with respect to the type of application and/or type of weed.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbidical compositions can be used. The active ingredient usually makes up from 0.5 to 90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid dilent medium. Typical of the liquid media commonly employed are methanol, benzene, toluene, and the like. The active ingredient usually makes up about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

The amount of active compound or composition administered will vary with the particular plant part or plant growth medium which is to be contacted, the general location of application—i.e., sheltered areas such as greenhouses, as compared to exposed areas such as fiels—as well as the desired type of control. Generally for both pre- and post-emergent herbidical control, the compounds of the invention are applied at rates of 0.2 to 60 kg/ha, and the preferred rate is in the range 0.5 to 40 kg/ha. For plant growth regulating or retarding activity, it is essential to apply the compounds at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Herbicidal tests on representative compounds of the invention were made using the following methods.

Pre-Emergent Herbicidal Test

An acetone solution of the test compound was prepared by mixing 375 mg of the compound, 118 mg of a nonionic surfactant and 18 ml of acetone. 10 ml of this solution was added to 40 ml of water to give the test solution.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

Post-Emergent Herbicidal Test

The test compound was formulated in the same manner as that described above for the pre-emergent test. This formulation was uniformly sprayed on 2 similar pots of 24-day-old plants (approximately 15 to 25 plants per pot) at a dose of 27.5 microgram/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

EXAMPLE 1

Preparation of 3-(2'-chloro-4'-trifluoromethyl-phenoxy)-phenol

A. To m-methoxyanisole (100 g) in DMSO (350 ml) was added 39 g sodium hydride (50%) in portions. The solution was stirred at room temperature under nitrogen overnight. 4-Trifluoromethyl-1,2-dichlorobenzene (173.2 g) was added to the solution in one portion, followed by copper powder (2 spatulas) and 18-crown ether (i,4,7,10,13,16-hexaoxacyclooctadecane, 2 g). The slurry was kept 152°–170° under nitrogen for 24 hours, then added to ice (1.5 l). The mixture was allowed to stand until the ice melted, then filtered. The solid which was collected was dissolved in methylene chloride (1.5 l) and filtered. The aqueous filtrate was extracted with methylene chloride (500 ml) and the methylene chloride phase was washed with water, dried (MgSO$_4$), filtered and stripped to yield a dark oil. The other methylene chloride solution (1.5 l) was washed with water, dried (MgSO$_4$), filtered and stripped to yield an oil. Both oil fractions were treated with petroleum ether and filtered. The filtrates were combined and stripped to yield the phenoxy methoxybenzene product, 244 g.

B. To the phenoxy methoxy benzene from A above (60.5 g) and sodium iodide (60 g) in acetonitrile (200 ml) was added trimethyl silane chloride (43.4 g). The slurry was refluxed under nitrogen for 24 hours.

The mixture was added to ice water (1.5 l) and stirred for one hour. Then 500 ml diethyl ether was added followed by solid sodium thiosulfate to remove the red color of the mixture. The yellow ether layer was collected, dried (MgSO$_4$), filtered and stripped to yield 60 g oil containing 83% of the title product.

EXAMPLE 2

Preparation of Ethyl 4-methyl-4-[3-(2'-chloro-4'-trifluoromethylphenoxy)-phenoxy]-crotonate To a stirred mixture of 3-(2'-chloro-4'-trifluoromethylphenoxy)-phenol (8.6 g) and potassium carbonate (4.5 g) in methyl ethyl ketone (150 ml) was added ethyl 4-bromo 2-pentenoate (8.6 g). The mixture was stirred for 2½ hours at room temperature under nitrogen, refluxed for 8 hours, then stirred at room temperature overnight. The mixture was filtered through MgSO$_4$ and the solids were washed with methyl ethyl ketone. The washings were added to the filtrate and stripped to yield a clear oil. The oil was chromtographed on silica gel (200 g) and eluted with pet. ether: diethyl ether. The fractions containing the title product were combined in methylene chloride and stripped to yield 10.5 g. (oil).

EXAMPLE 3

Preparation of 4-methyl-4-[3-(2'-chloro-4-trifluoromethylphenoxy)phenoxy]-crotonic acid The ester from Example 2 was dissolved in 100 ml methanol and 40 ml of 15% sodium hydroxide solution was added. After stirring overnight, the methanol was stripped. The solution was acidified with 25% HCl and extracted with methylene chloride. The extract was dried (MgSO$_4$), filtered and stripped to yield the title product.

EXAMPLE 4

Preparation of N-isopropyl 4-methyl-4-[3-(2'-chloro-4'-trifluoromethylphenoxy)-phenoxy]-crotonamide The acid (2 g) from Example 3 was dissolved in methylene chloride (50 ml) and oxalyl chloride (2 g) was added. The solution was stirred overnight at room temperature. The solution was placed under vacuum to remove hydrogen chloride and excess oxalyl chloride. A solution of isopropylamine in 50 ml methylene chloride was added and the mixture was stirred for one hour then refluxed for one hour. The solution was washed with water, dried (MgSO$_4$), filtered and stripped. The residue was diluted with ether, filtered, stripped, and chromatographed on silica gel (150 g). Elution with 5% hexane:25% diethyl ether:pet. ether yielded the title product, 1.0 g.

TABLE I

COMPOUNDS OF THE FORMULA

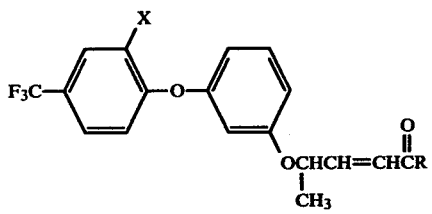

| No. | R | X | mp °C. | C Cal. | C Fd. | H Cal. | H Fd. | N Cal. | N Fd. |
|---|---|---|---|---|---|---|---|---|---|
| 1 | $OC_2H_5$ | Cl | Oil | 57.91 | 57.7 | 4.37 | 4.22 | | |
| 2 | OH | Cl | Oil | 55.89 | 56.72 | 3.65 | 4.16 | | |
| 3 | $OC_2H_5$ | H | Oil | 63.15 | 60.09 | 5.04 | 5.73 | | |
| 4 | OH | H | Oil | 61.54 | 58.51 | 4.02 | 4.68 | | |
| 5 | $NHCH(CH_3)_2$ | Cl | 104-107 | 58.95 | 59.99 | 4.95 | 5.36 | 3.27 | 3.35 |

TABLE II

HERBICIDAL ACTIVITY

| | Pre/Post | | % Control | | | |
|---|---|---|---|---|---|---|
| No. | L | M | P | C | W | O |
| 1 | 90/35 | 60/70 | 70/70 | 0/0 | 0/0 | 0/0 |
| 2 | 70/48 | 70/58 | 90/58 | 0/0 | 0/25 | 0/0 |
| 3 | 0/28 | 0/48 | 0/25 | 0/0 | 35/0 | 0/0 |
| 4 | 0/20 | 0/45 | 0/25 | 0/0 | 0/0 | 0/0 |
| 5 | 0/10 | 0/20 | 0/30 | 0/0 | 0/0 | 0/0 |

L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
O = Wild Oats (*Avenua fatua*)

What is claimed is:

1. A compound of the formula (I):

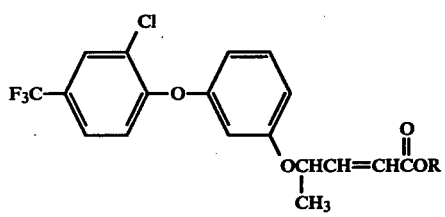

(I)

wherein R is hydrogen, alkyl of 1 to 6 carbon atoms or a monovalent inorganic cation or quaternary ammonium cation.

2. A compound according to claim 1 wherein R is alkoxy of 1 to 6 carbon atoms.

3. The compound according to claim 3 wherein R is ethyl.

4. The compound according to claim 1 wherein R is hydrogen.

5. A method for the control of broadleaf vegetation which comprises applying to said vegetation or its habitat an herbicidally effective amount of a compound of the formula defined in claim 1.

6. An herbicidal composition comprising a biologically inert carrier and an herbicidally effective amount of a compound of the formula defined in claim 1.

7. A method for the control of broadleaf vegetation which comprises applying to said vegetation or its habitat an herbicidally effective amount of a compound of the formula defined in claim 3.

8. An herbicidal composition comprising a biologically inert carrier and an herbicidally effective amount of a compound of the formula defined in claim 3.

9. A method for the control of broadleaf vegetation which comprises applying to said vegetation or its habitat an herbicidally effective amount of a compound of the formula defined in claim 4.

10. An herbicidal composition comprising a biologically inert carrier and an herbicidally effective amount of a compound of the formula defined in claim 4.